(12) United States Patent
Handa et al.

(10) Patent No.: US 9,149,654 B2
(45) Date of Patent: Oct. 6, 2015

(54) RADIOTHERAPY DEVICE CONTROLLER AND METHOD OF MEASURING POSITION OF SPECIFIC-PART

(75) Inventors: Takanobu Handa, Tokyo (JP); Kunio Takahashi, Tokyo (JP); Kenji Takayama, Tokyo (JP); Takashi Mizowaki, Kyoto (JP); Masahiro Hiraoka, Kyoto (JP); Yuichiro Narita, Hirosaki (JP)

(73) Assignees: MITSUBISHI HEAVY INDUSTRIES, LTD., Tokyo (JP); KYOTO UNIVERSITY, Kyoto (JP)

( * ) Notice: Subject to any disclaimer, the term of this patent is extended or adjusted under 35 U.S.C. 154(b) by 463 days.

(21) Appl. No.: 13/501,261

(22) PCT Filed: Nov. 12, 2010

(86) PCT No.: PCT/JP2010/070203
§ 371 (c)(1),
(2), (4) Date: Apr. 11, 2012

(87) PCT Pub. No.: WO2011/059061
PCT Pub. Date: May 19, 2011

(65) Prior Publication Data
US 2012/0199760 A1   Aug. 9, 2012

(30) Foreign Application Priority Data
Nov. 16, 2009   (JP) ................. 2009-260614

(51) Int. Cl.
*G06K 9/00* (2006.01)
*A61N 5/10* (2006.01)

(52) U.S. Cl.
CPC ....... *A61N 5/1049* (2013.01); *A61N 2005/1056* (2013.01); *A61N 2005/1061* (2013.01)

(58) Field of Classification Search
None
See application file for complete search history.

(56) References Cited

U.S. PATENT DOCUMENTS

| | | |
|---|---|---|
| 2006/0074292 A1 | 4/2006 | Thomson et al. |
| 2007/0211857 A1 | 9/2007 | Urano et al. |
| 2007/0237290 A1 | 10/2007 | Mostafavi |

(Continued)

FOREIGN PATENT DOCUMENTS

| | | |
|---|---|---|
| JP | 2001-259059 | 9/2001 |
| JP | 2007-507275 | 3/2007 |

(Continued)

OTHER PUBLICATIONS

Multileaf collimator, Wikipedia: the free encyclopedia, Jul. 6, 2008.*

(Continued)

*Primary Examiner* — Stephen R Koziol
*Assistant Examiner* — Raphael Schwartz
(74) *Attorney, Agent, or Firm* — Wenderoth, Lind & Ponack, L.L.P.

(57) ABSTRACT

A radiotherapy device controller includes: a visual line calculator configured to calculate a visual line based on a position on a transmissive image imaged using a radiation penetrating a subject, a specific part of the subject being shown at the position; a position calculator configured to calculate a position of the specific part based on a position of a trajectory of the specific part and a position of the visual line; and an emitter configured to control a radiation emitter that emits a therapeutic radiation, so that the therapeutic radiation penetrates at the position of the specific part.

20 Claims, 8 Drawing Sheets

(56) References Cited

U.S. PATENT DOCUMENTS

| | | |
|---|---|---|
| 2007/0244386 A1 | 10/2007 | Steckner et al. |
| 2008/0039713 A1 | 2/2008 | Thomson et al. |
| 2009/0180666 A1* | 7/2009 | Sheng et al. ............ 382/103 |

FOREIGN PATENT DOCUMENTS

| | | |
|---|---|---|
| JP | 2007-236729 | 9/2007 |
| JP | 2007-236760 | 9/2007 |
| JP | 4064952 | 3/2008 |
| JP | 2008-514352 | 5/2008 |
| JP | 2009-533086 | 9/2009 |

OTHER PUBLICATIONS

Sterner, R, Johns Hopkins University Applied Physics Laboratory, Dec. 30, 1986.*

International Search Report issued Dec. 14, 2010 in International (PCT) Application No. PCT/JP2010/070203.

Written Opinion of the International Searching Authority issued Dec. 14, 2010 in International (PCT) Application No. PCT/JP2010/070203.

Supplementary European Search Report dated Apr. 17, 2013 in corresponding European Patent Application No. 10830020.3.

* cited by examiner

RADIOTHERAPY DEVICE CONTROLLER AND METHOD OF MEASURING POSITION OF SPECIFIC-PART

TECHNICAL FIELD

The present invention relates to a radiotherapy device controller and a method of measuring the position of a specific part. Particularly, the present invention relates to a radiotherapy device controller and a method of measuring the position of a specific part, which are used when treating by radiotherapy an affected part of tumor inside a human body.

Priority is claimed on Japanese Patent Application No. 2009-260614, filed Nov. 16, 2009, the content of which is incorporated herein by reference.

BACKGROUND ART

Radiotherapy for treating a patient by emitting therapeutic radiation to an affected part (tumor) has been well known. A high therapeutic effect is demanded for the radiotherapy. Regarding the radiation, the dose of radiation to be emitted to a normal cell is preferably lower than the dose of radiation to be emitted to a cell of the affected part. For this reason, it is necessary to precisely emit therapeutic radiation to the affected part. A radiotherapy device that performs radiotherapy includes: an imaging system that images a transmissive image of a patient; a therapeutic radiation emitter that emits therapeutic radiation; and a driver that drives the therapeutic radiation emitter. The radiotherapy device calculates the position of the affected part based on the transmissive image, and drives the therapeutic radiation emitter by using the driver so that therapeutic radiation is emitted to the position.

A support structure for supporting the therapeutic radiation emitter and the imaging system is deflected under the weight of the support structure itself or the therapeutic radiation emitter thereof. For this reason, when the support structure is moved, the transmissive image of the patient shows another visual field deviated from the desired visual field in some cases. In this case, a user is given erroneous information when determining the position of a subject to be irradiated or when confirming the precision of position determination. It has been demanded to precisely determine the position of a subject to be irradiated and to confirm the precision of position determination.

Japanese Unexamined Patent Application, First Publication No. 2001-259059 discloses an affected-part tracking method that precisely tracks respiratory displacement of an affected part. The affected-part tracking method for tracking a displacement of the affected part is characterized in that an optical flow is calculated from transmissive images of a periphery of the affected part, flow vectors thereof are combined, and thereby calculating a motion vector of the affected part.

Japanese Patent Publication No. 4064952 discloses a radiation emitter that can properly emit therapeutic radiation to a subject to be irradiated. The radiotherapy device is a radiotherapy device for emitting therapeutic radiation to an affected part of a patient positioned at the isocenter. The radiotherapy device includes: a plurality of transmissive-image radiation generator provided on a rotation member rotatable about an rotation axis passing through the isocenter; a plurality of image detectors configured to detect transmissive image radiation emitted from each of the plurality of transmissive-image radiation generator and to detect an image of the affected part positioned between the transmissive-image radiation generators; a therapeutic radiation generator provided on the rotation member and configured to emit therapeutic radiation to the affected part; a moving means configured to move the therapeutic radiation generator with respect to the rotation member; a time-series data processor configured to calculate an estimated position of the affected part based on each of the transmissive image data imaged in chronological order by the plurality of transmissive-image radiation generator and the plurality of image detectors; an analyzer configured to calculate displacement for moving the irradiation axis of the therapeutic radiation generator to the estimated position of the affected part based on the information of the estimated position of the affected part; and a controller configured to control the moving means so as to move the irradiation axis of the therapeutic radiation generator to the estimated position of the affected part based on the information of the displacement. The controller is configured to control the plurality of transmissive-image radiation generators such that two of the plurality of transmissive-image radiation generators do not simultaneously emit the transmissive image radiation to the affected part positioned at the isocenter.

Japanese Unexamined Patent, First Publication No. 2007-236760 discloses a radiotherapy device controller that properly emits radiation to part of a moving subject. The radiotherapy device controller is a radiotherapy device controller configured to control a radiotherapy device including: a therapeutic radiation emitter configured to emit therapeutic radiation to part of the subject; a motion detector configured to detect a motion of the subject; and a driver configured to move the therapeutic radiation emitter with respect to the subject. The radiotherapy device controller includes: an affected-part database configured to correlate a set of motions with a set of positions; a motion collector configured to collect a motion from the motion detector; and an irradiation position controller configured to move, using the driver, the therapeutic radiation emitter so that the therapeutic radiation is emitted to the position of the set of positions which is correlated with the motion.

CITATION LIST

Patent Document

[Patent Document 1] Japanese Unexamined Patent Application, First Publication No. 2001-259059
[Patent Document 2] Japanese Patent Publication No. 4064952
[Patent Document 3] Japanese Unexamined Patent Application, First Publication No. 2007-236760

DISCLOSURE OF THE INVENTION

Problems to be Solved by the Invention

The present invention provides a radiotherapy device controller and a method of measuring the position of a specific part, which more precisely measure a specific part positioned inside a subject.

The present invention provides a radiotherapy device controller and a method of measuring the position of a specific part, which reduce the exposed level of radiation emitted to the subject when more precisely measuring the specific part positioned inside the subject.

Means for Solving the Problems

Hereinafter, means for solving the problems is described using reference numerals in parentheses, which are used in the best mode for carrying out the invention and the embodiments. These reference numerals are appended in order to clarify the relationship between the claims and the description of the best mode for carrying out the invention and the embodiments. These reference numerals must not be used to interpret the technical scope of the claimed invention.

A radiotherapy device controller (2) according to the present invention includes: a visual line calculator (53) configured to calculate a visual line (72) based on a position on a transmissive image imaged using a radiation (35, 36) penetrating a subject (43), a specific part (60) of the subject (43) being shown at the position; a position calculator (55) configured to calculate a position of the specific part (74, 75, 76) (84, 85, 86) (93, 94, 95) based on a position of a trajectory (71) (82) (91) of the specific part (60) and a position of the visual line (72); and an emitter (58) configured to control a radiation emitter (16) that emits a therapeutic radiation (23), so that the therapeutic radiation (23) penetrates at the position of the specific part (74, 75, 76) (84, 85, 86) (93, 94, 95).

The above radiotherapy device controller (2) can more precisely calculate, using a transmissive image, the position of the specific part (74, 75, 76) (84, 85, 86) (93, 94, 95) at which the specific part (60) disposed inside the subject (43) is disposed. Accordingly, the above radiotherapy device controller (2) can reduce, when calculating the position of the specific part (74, 75, 76) (84, 85, 86) (93, 94, 95), the exposed level of radiation (35, 36) emitted to the subject (43).

The position of the specific part (74, 75, 76) (84, 85, 86) (93, 94, 95) indicates a position of a third point included in a line segment connecting a first point (74) (84) (93) and a second point (75) (85) (94). The first point (74) (84) (93) is included in the trajectory (71) (82) (91) and is the closest to the visual line (72). The second point (75) (85) (94) is included in the visual line (72) and is the closest to the trajectory (71) (82) (91).

The trajectory (82) is formed to be a line segment. If the line segment of the trajectory (82) is not parallel to the visual line (72), the first point (84), which is included in the trajectory (82) and is closest to the visual line (72), is determined uniquely. Additionally, the second point (85), which is included in the visual line (72) and is closest to the trajectory (82), is determined uniquely. For this reason, the position of the specific part (84, 85, 86) can be calculated more precisely.

The radiotherapy device controller (2) according to the present invention further includes: a trajectory model generator (51) configured to calculate the trajectory (71) (82) (91) based on a plurality of first transmissive images and a plurality of second transmissive images, the plurality of first transmissive images being imaged at a plurality of times different from one another by using a radiation (35) emitted from a first position, and the plurality of second transmissive images being imaged at the plurality of times by using a radiation (36) emitted from a second position different from the first position.

The radiotherapy device controller (2) according to the present invention further includes: a surrogate signal acquirer (54) configured to collect a plurality of surrogate signal values measured at the plurality of times the plurality of transmissive images are imaged. The position calculator (55) is configured to refer to a table (65) that correlates a set of surrogate signal values (66) with a set of partial trajectories (67), and to calculate from the set of partial trajectories (67), a partial trajectory (92) correlated with one of the plurality of surrogate signal values. The trajectory (91) includes the partial trajectory (92). The position of the specific part (93, 94, 95) indicates a position of a third point included in a line segment connecting a first point (93) and a second point (94).

The first point (93) is included in the partial trajectory (92) and is the closest to the visual line (72). The second point (94) is included in the visual line (72) and is the closest to the partial trajectory (92). If the trajectory (91) is a curve, there are occasionally a plurality of points which are included in the trajectory (91) and are closest to the visual line (72), and there are occasionally a plurality of points which are included in the visual line (72) and are closest to the trajectory (91). According to the above radiotherapy device controller (2), the probability that there will be a plurality of first points (93) or second points (94) is reduced, and thereby the position of the specific position (93, 94, 95) can be calculated more precisely.

The radiotherapy device controller (2) according to the present invention further includes: a surrogate signal acquirer (54) configured to collect a plurality of surrogate signal values measured at the plurality of times the plurality of transmissive images are imaged. The position calculator (55) is configured to refer to a table (65) that correlates a set of surrogate signal values (66) with a set of positions (67), and to calculate a first point (74) (84) (93) that is included in the set of positions (67) and is correlated with one of the plurality of surrogate signal values. In this case, the position of the specific part (75, 76) (85, 86) (94, 95) indicates a position of a third point included in a line segment connecting the first point (74) (84) (93) and a second point (75) (85) (94). The second point (75) (85) (94) is included in the visual line (72) and is the closest to the first point (74) (84) (93). The third point differs from the first point (74) (84) (93).

Each of the plurality of surrogate signal values indicates a position of a marker (61) on the subject (43), and the marker (61) differs from the specific part (60).

As the position of the specific part (74, 75, 76) (84, 85, 86) (93, 94, 95), the position of a point, which is selected from the first point (74) (84) (93), the second point (75) (85) (94), and the third point based on the information input by an input device being operated, may be used. In this case, the third point differs from the first point (74) (84) (93), and differs from the second point (75) (85) (94).

The radiotherapy device controller (2) according to the present invention further includes: a driver (56) configured to drive, based on the position of the specific part (74, 75, 76) (84, 85, 86) (93, 94, 95), a driving device (15) that drives the radiation emitter (16), so that the therapeutic radiation (23) penetrates at the position of the specific part (74, 75, 76) (84, 85, 86) (93, 94, 95).

The emitter (58) is configured to calculate a region (89) (97) based on a previous position of the specific part (88-1 to 88-3) (96-1 to 96-3) calculated before the position of the specific part is calculated. The emitter (58) is configured to control the radiation emitter (16) so as not to emit the therapeutic radiation (23) if the position of the specific part is not included in the region (89) (97).

The radiotherapy device controller (2) according to the present invention further includes: an irradiated-filed shape controller (57) configured to control, based on the transmissive image, an irradiated-filed shape control device (20) that partially blocks the therapeutic radiation (23), so that a shape of an irradiated filed of the therapeutic radiation (23) emitted to the subject (43) is updated.

A method of measuring a position of a specific part according to the present invention includes: a step of calculating a visual line (72) based on a position on a transmissive image imaged using a radiation (33, 36) penetrating a subject (43), a specific part (60) of the subject (43) being shown at the position; and a step of calculating a position of the specific part based on a position of a trajectory (71) (82) (91) of the specific part (60) and a position of the visual line (72). The above method of measuring the position of the specific part enables, with use of a transmissive image, more precise calculation of the position of the specific part at which the specific part (60) disposed inside the subject (43) is disposed. Accordingly, the above method of measuring the position of the specific part enables a reduction in the exposed level of radiation (35, 36) emitted to the subject (43), when the position of the specific part is calculated.

The position of the specific part indicates a position of a third point included in a line segment connecting a first point (74) (84) (93) and a second point (75) (85) (94). The first point (74) (84) (93) is included in the trajectory (71) (82) (91) and is the closest to the visual line (72). The second point (75) (85) (94) is included in the visual line (72) and is the closest to the trajectory (71) (82) (91).

Preferably, the trajectory (82) is formed to be a line segment. If the line segment of the trajectory (82) is not parallel to the visual line (72), the first point (84), which is included in the trajectory (82) and is the closest to the visual line (72), is determined uniquely. Additionally, the second point (85), which is included in the visual line (72) and is the closest to the trajectory (82), is determined uniquely. For this reason, the position of the specific part can be calculated more precisely.

The method of measuring the position of the specific part according to the present invention further includes: a step of calculating the trajectory (71) (82) (91) based on a plurality of first transmissive images and a plurality of second transmissive images, the plurality of first transmissive images being imaged at a plurality of times different from one another by using a radiation (35, 36) emitted from a first position, and the plurality of second transmissive images being imaged at the plurality of times by using a radiation (35, 36) emitted from a second position different from the first position.

The method of measuring the position of the specific part according to the present invention further includes: a step of generating a table (65) that correlates a set of surrogate signal values (66) with a set of partial trajectories, based on the trajectory (91) and a plurality of surrogate signal values measured at the plurality of times; a step of collecting a plurality of surrogate signal values measured at the plurality of times the plurality of transmissive images are imaged; and a step of calculating from the set of partial trajectories, a partial trajectory (92) correlated with one of the plurality of surrogate signal values. The position of the specific part indicates a position of a third point included in a line segment connecting a first point (93) and a second point (94). The first point (93) is included in the partial trajectory (92) and is the closest to the visual line (72). The second point (94) is included in the visual line (72) and is the closest to the partial trajectory (92). If the trajectory (91) is a curve, there are occasionally a plurality of points which are included in the trajectory (91) and are the closest to the visual line (72), and there are occasionally a plurality of points which are included in the visual line (72) and are the closest to the trajectory (91). According to the above method of measuring the position of the specific part, the probability that there will be a plurality of first points (93) or second points (94) is reduced, and thereby the position of the specific position can be calculated more precisely.

The method of measuring the position of the specific part according to the present invention further includes: a step of generating a table (65) that correlates a set of surrogate signal values (66) with a set of positions (67), based on the trajectory (71) (82) (91) and a plurality of surrogate signal values measured at the plurality of times; a step of collecting a plurality of surrogate signal values measured at the plurality of times the plurality of transmissive images are imaged; and a step of calculating a first point (74, 84, 93) that is included in the set of positions (67) and is correlated with one of the plurality of surrogate signal values. The position of the specific part indicates a position of a third point included in a line segment connecting the first point (74) (84) (93) and a second point (75) (85) (94). The second point (75) (85) (94) is included in the visual line (72) and is the closest to the first point (74) (84) (93). The third point differs from the first point (74) (84) (93).

Preferably, each of the plurality of surrogate signal values indicates a position of a marker (61) on the subject (43), and the marker (61) differs from the specific part (60).

As the position of the specific part, the position of a point, which is selected from the first point (74) (84) (93), the second point (75) (85) (94), and the third point based on the information input by an input device being operated, may be used. In this case, the third point differs from the first point (74) (84) (93), and differs from the second point (75) (85) (94).

A radiation emitting method according to the present invention includes: a step of performing the method of measuring the position of the specific part according to the present invention; and a step of driving a radiation emitter (16) that emits a therapeutic radiation (23), with respect to the subject (43), so that the therapeutic radiation (23) penetrates at the position of the specific part.

Preferably, the radiation emitting method according to the present invention further includes: a step of calculating a region (89) (97) based on a previous position of the specific part (88-1 to 88-3) (96-1 to 96-3) calculated before calculating the position of the specific part, the previous position being calculated by the method of measuring the position of the specific part; and a step of controlling the radiation emitter (16) so as not to emit the therapeutic radiation (23) if the position of the specific part is not included in the region (89) (97).

Preferably, the radiation emitting method according to the present invention further includes: a step of controlling, based on the transmissive image, an irradiated-filed shape control device (20) that partially blocks the therapeutic radiation (23), so that a shape of an irradiated filed of the therapeutic radiation (23) emitted to the subject (43) is updated.

Effects of the Invention

The radiotherapy device controller and the method of measuring the position of a specific part according to the present invention can more precisely measure the position of a specific part positioned inside a subject.

The radiotherapy device controller and the method of measuring the position of a specific part according to the present invention can further reduce, when calculating the position of the specific part by using one transmissive image, the exposed level of radiation emitted to the subject, compared to the technique of calculating the position of the specific part by using a plurality of transmissive images.

BEST MODE FOR CARRYING OUT THE INVENTION

Figure 1:
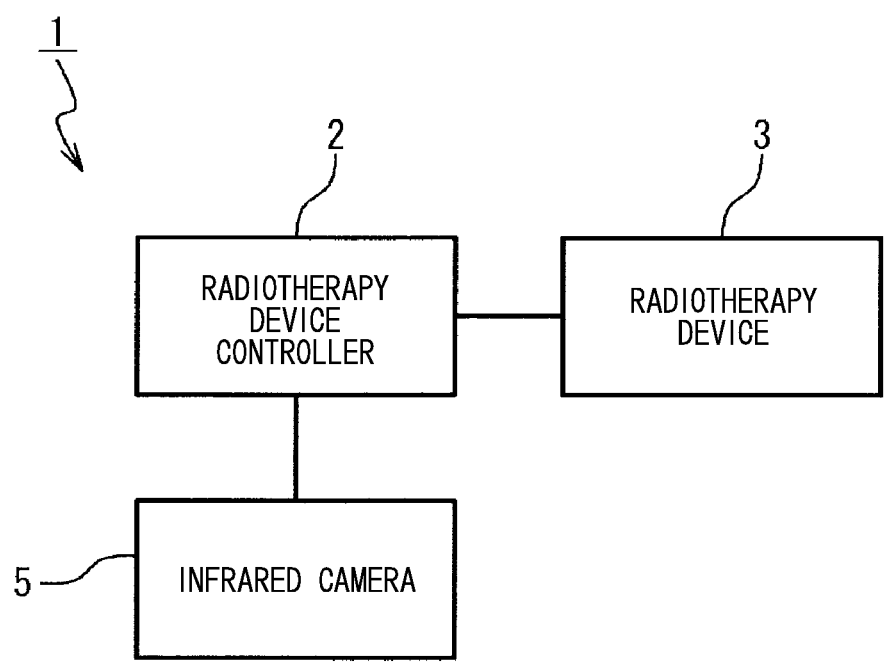
FIG. 1 is a block diagram illustrating a radiotherapy system according to a first embodiment of the present invention.

Embodiments of a radiotherapy device controller according to the present invention are explained with reference to the drawings. As shown in FIG. 1, a radiotherapy device controller 2 is applied to a radiotherapy system 1. The radiotherapy system 1 includes: the radiotherapy device controller 2; a radiotherapy device 3; and an infrared camera 5. The radiotherapy device controller 2 is a computer, such as a personal computer. The radiotherapy device controller 2, the radiotherapy device 3, and the infrared camera 5 are connected to one another so as to bilaterally transfer information. The infrared camera 5 is configured to image an infrared image of a patient by using a reflected light of radiation emitted to the patient, and to output the infrared image to the radiotherapy device controller 2.

Figure 2:
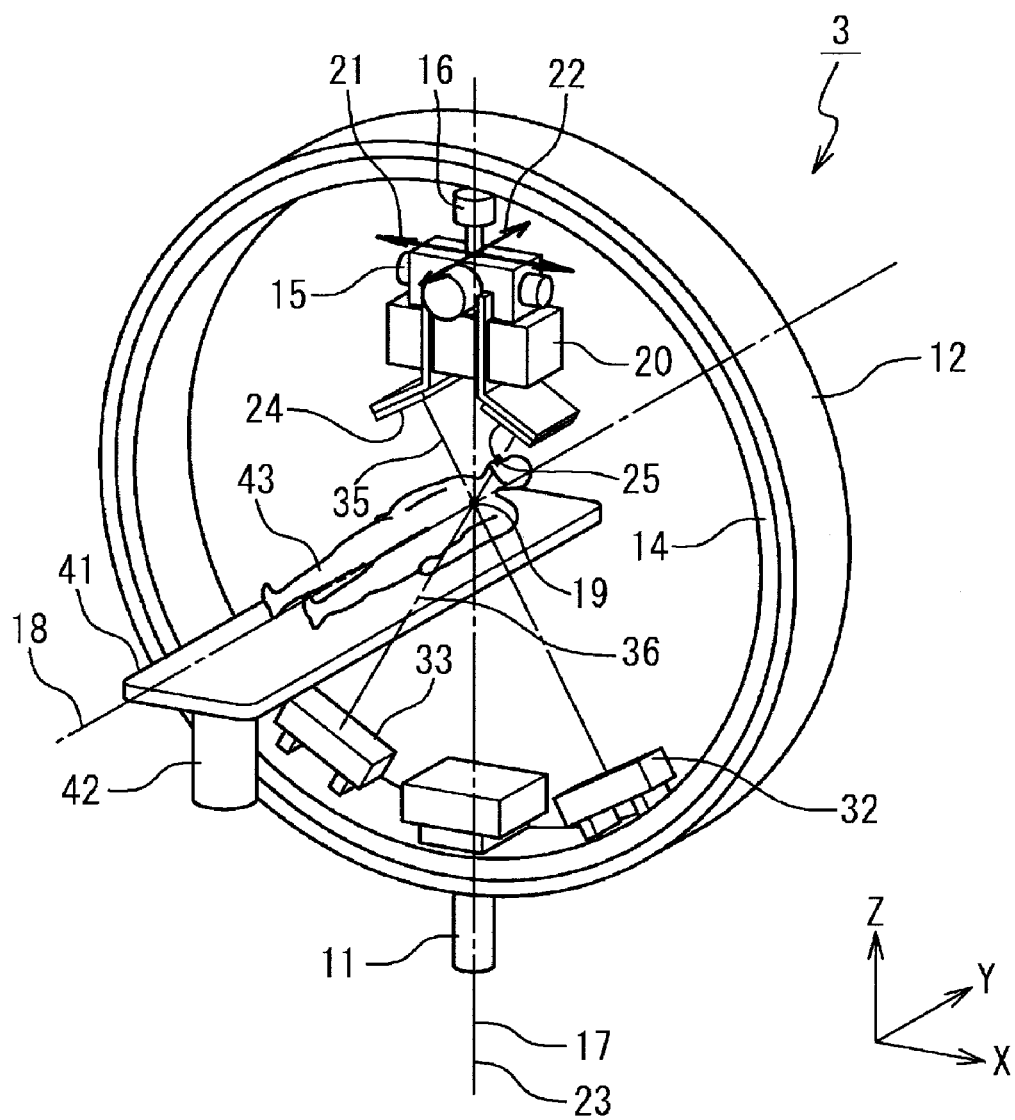
FIG. 2 is a perspective view illustrating a radiotherapy device according to the first embodiment of the present invention.

FIG. 2 illustrates the radiotherapy device 3. The radiotherapy device 3 includes: a rotation driver 11; an O-ring 12; a travel gantry 14; a swing mechanism 15; and a therapeutic radiation emitter 16. The rotation driver 11 supports the O-ring 12 on a base while being rotatable about a rotation axis 17. Under control of the radiotherapy device controller 2, the rotation driver 11 rotates the O-ring 12 about the rotation axis 17. The rotation axis 17 is parallel to a vertical direction. The rotation driver 11 measures a rotation angle of the O-ring 12 with respect to the base. The O-ring 12 is formed in the shape of a ring with respect to the rotation axis 18 regarded as an axis. The O-ring 12 is rotatable about the rotation axis 18 while supporting the travel gantry 14. The rotation axis 18 is orthogonal to the vertical direction. The rotation axis 18 passes through an isocenter 19 included in the rotation axis 17. Further, the rotation axis 18 is fixed onto the O-ring 12, that is, rotates about the rotation axis 17 together with the O-ring 12. The travel gantry 14 is formed in the shape of a ring with respect to the rotation axis 18 regarded as the center. The travel gantry 14 and the O-ring 12 are arranged in a concentric pattern. The radiotherapy device 3 further includes a travel driver that is not shown. Under control of the radiotherapy device controller 2, the travel driver rotates the travel gantry 14 about the rotation axis 18. Further, the travel driver measures a travel angle of the travel gantry 14 with respect to the O-ring 12.

The swing mechanism 15 fixes the therapeutic radiation emitter 16 to the travel gantry 14 so that the therapeutic radiation emitter 16 is disposed inside the travel gantry 14. The swing mechanism 15 includes a tilt axis 21 and a pan axis 22. The pan axis 22 is fixed with respect to the travel gantry 14. The pan axis 22 is parallel to the rotation axis 18 without crossing the rotation axis 18. The tilt axis 21 is orthogonal to the pan axis 22. Under control of the radiotherapy device controller 2, the swing mechanism 15 rotates the therapeutic radiation emitter 16 about the pan axis 22, and rotates the therapeutic radiation emitter 16 about the tilt axis 21.

The therapeutic radiation emitter 16 emits therapeutic radiation 23 under control of the radiotherapy device controller 2. The therapeutic radiation 23 is emitted substantially along a straight line passing the intersection of the pan axis 22 with the tilt axis 21. The therapeutic radiation 23 is formed so as to have a uniform intensity distribution. The therapeutic radiation emitter 16 includes a multileaf collimator (MLC) 20. Under control of the radiotherapy device controller 2, the multileaf collimator 20 blocks part of the therapeutic radiation 23, thereby changing the shape of an irradiated field when the therapeutic radiation 23 is emitted to a patient.

When the therapeutic radiation emitter 16 is fixed to the travel gantry 14 in the above manner, and thereby the therapeutic radiation emitter 16 is adjusted by the swing mechanism 15 so as to face an isocenter 19, the therapeutic radiation 23 substantially always passes through the isocenter 19, even if the O-ring 12 is rotated by the rotation driver 11, or the travel gantry 14 is rotated by the travel driver. In other words, traveling and rotating enables emission of the therapeutic radiation 23 toward the isocenter 19 from an arbitrary direction.

The radiotherapy device 3 further includes a plurality of imaging systems. In other words, the radiotherapy device 3 includes: diagnostic X-ray sources 24 and 25; and sensor arrays 32 and 33. The diagnostic X-ray source 24 is fixed to the travel gantry 14. The diagnostic X-ray source 24 is disposed inside the ring of the travel gantry 14 such that a line segment connecting the isocenter 19 and the diagnostic X-ray source 24 makes an acute angle with a line segment connecting the isocenter 19 and the therapeutic radiation emitter 16. Under control of the radiotherapy device controller 2, the diagnostic X-ray source 24 emits a diagnostic X-ray 35 toward the isocenter 19. The diagnostic X-ray 35 is emitted from one point of the diagnostic X-ray source 24, and is a cone beam in conical shape having a vertex at the one point. The diagnostic X-ray source 25 is fixed to the travel gantry 14. The diagnostic X-ray source 25 is disposed inside the ring of the travel gantry 14 such that a line segment connecting the isocenter 19 and the diagnostic X-ray source 25 makes an acute angle with a line segment connecting the isocenter 19 and the therapeutic radiation emitter 16. Under control of the radiotherapy device controller 2, the diagnostic X-ray source 25 emits a diagnostic X-ray 36 toward the isocenter 19. The diagnostic X-ray 36 is emitted from one point of the diagnostic X-ray source 25, and is a cone beam in conical shape having a vertex at the one point.

The sensor array 32 is fixed to the travel gantry 14. The sensor array 32 receives the diagnostic X-ray 35 emitted from the diagnostic X-ray source 24 and penetrating a subject around the isocenter 19, and generates a transmissive image of the subject. The sensor array 33 is fixed to the travel gantry 14. The sensor array 33 receives the diagnostic X-ray 36 emitted from the diagnostic X-ray source 25 and penetrating the subject around the isocenter 19, and generates a transmissive image of the subject. For example, an FPD (Flat Panel Detector) or an X-ray II (Image Intensifier) is used as the sensor arrays 32 and 33.

According to the above imaging systems, transmissive images in which the isocenter 19 is regarded as the center can be generated based on the image signals obtained from the sensor arrays 32 and 33.

The radiotherapy device 3 further includes: a couch 41; and a couch driver 42. The couch 41 is used by a patient 43 to be treated by the radiotherapy system 1 lying thereon. The couch 41 includes a fixator that is not shown. The fixator fixes the patient onto the couch 41 so that the patient does not move. The couch driver 42 fixes the couch 41 to the base, and moves the couch 41 under control of the radiotherapy device controller 2.

Figure 3:
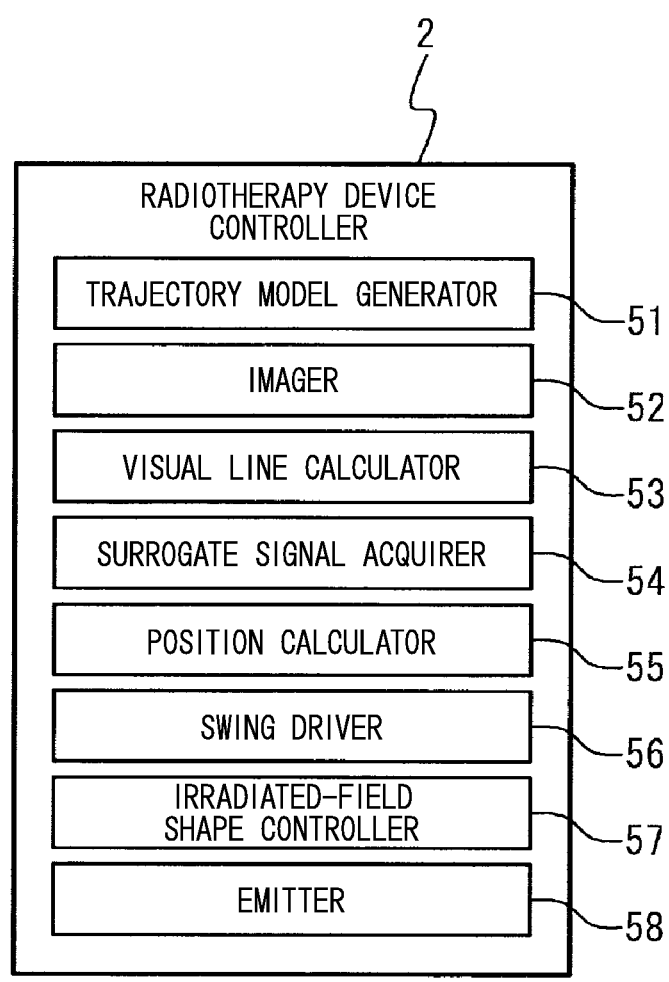
FIG. 3 is a block diagram illustrating a radiotherapy device controller according to the first embodiment of the present invention.

FIG. 3 illustrates the radiotherapy device controller 2. The radiotherapy device controller 2 includes a CPU, a storing device, an input device, and an interface, which are not shown. The CPU executes a computer program to be installed in the radiotherapy device controller 2, and controls the storing device, the input device, and the interface. The storing device stores the computer program, and temporarily stores information generated by the CPU. The input device generates information by user operation, and outputs the information to the CPU. The input device includes, for example, a keyboard. The interface outputs, to the CPU, information generated by an external device connected to the radiotherapy device controller 2. Then, the interface outputs the information generated by the CPU to the external device. The external device includes: the rotation driver 11, the travel driver, the swing mechanism 15, the therapeutic radiation emitter 16, the multileaf collimator 20, the imaging systems (the diagnostic X-ray sources 24 and 25, and the sensor arrays 32 and 33), and the couch driver 42, which are included in the radiotherapy device 3.

The computer program includes: a trajectory model generator 51; an imager 52; a visual line calculator 53; a surrogate signal acquirer 54; a position calculator 55; a swing driver 56; an irradiated-field shape controller 57; and an emitter 58.

The trajectory model generator 51 fixes the O-ring 12 at a predetermined rotation angle by using the rotation driver 11 of the radiotherapy device 3. The trajectory model generator 51 fixes the travel gantry 14 at a predetermined travel angle by using the travel driver of the radiotherapy device 3. While the travel gantry 14 is fixed, the trajectory model generator 51 images, using the imaging systems of the radiotherapy device 3, a plurality of transmissive images of the patient 43 at a plurality of different imaging times. Then, the trajectory model generator 51 correlates the plurality of transmissive images with the plurality of imaging times, and stores in the storing unit, the plurality of transmissive images correlated with the plurality of imaging times. Additionally, the trajectory model generator 51 images, using the infrared camera 5, a plurality of infrared images of the patient 43 at the plurality of imaging times. Then, the trajectory model generator 51 correlates the plurality of infrared images with the plurality of imaging times, and stores in the storing unit, the plurality of infrared images correlated with the plurality of imaging times. Further, the trajectory model generator 51 calculates, based on the plurality of transmissive images, a trajectory of the affected part of the patient 43 which moves by the patient 43 breathing. Moreover, the trajectory model generator 51 calculates, based on the plurality of transmissive images and the plurality of infrared images, a surrogate table indicating the relationship between surrogate signal values calculated from the infrared images imaged by the infrared camera 5, and the positions of the affected part of the patient 43.

The imager 52 images transmissive images of the patient 43 by using the imaging systems of the radiotherapy device 3.

The visual line calculator 53 calculates a visual line based on the transmissive images imaged by the imager 52.

The surrogate signal acquirer 54 images, using the infrared camera 5, an infrared image of the patient 43 at the time that the transmissive image is imaged by the imager 52. Additionally, the surrogate signal acquirer 54 generates a surrogate signal value by image-processing the infrared image.

The position calculator calculates the position of the affected part of the patient 43 based on the information input by the user through the input device, the surrogate table generated by the projector model generator 51, the visual line calculated by the visual line calculator 53, and the surrogate signal generated by the surrogate signal acquirer 54.

The swing driver 56 drives the therapeutic radiation emitter 16 by using the swing mechanism 15 so that the therapeutic radiation 23 penetrates the position of the affected part calculated by the position calculator 55. The irradiated-field shape controller 57 calculates the shape of the irradiated field based on the transmissive images imaged by the imager 52, and controls the multileaf collimator 20 so that the irradiated field of the therapeutic radiation 23 is formed in the calculated shape. The emitter 58 emits the therapeutic radiation 23 to a patient by using the therapeutic radiation emitter 16.

Figure 4:
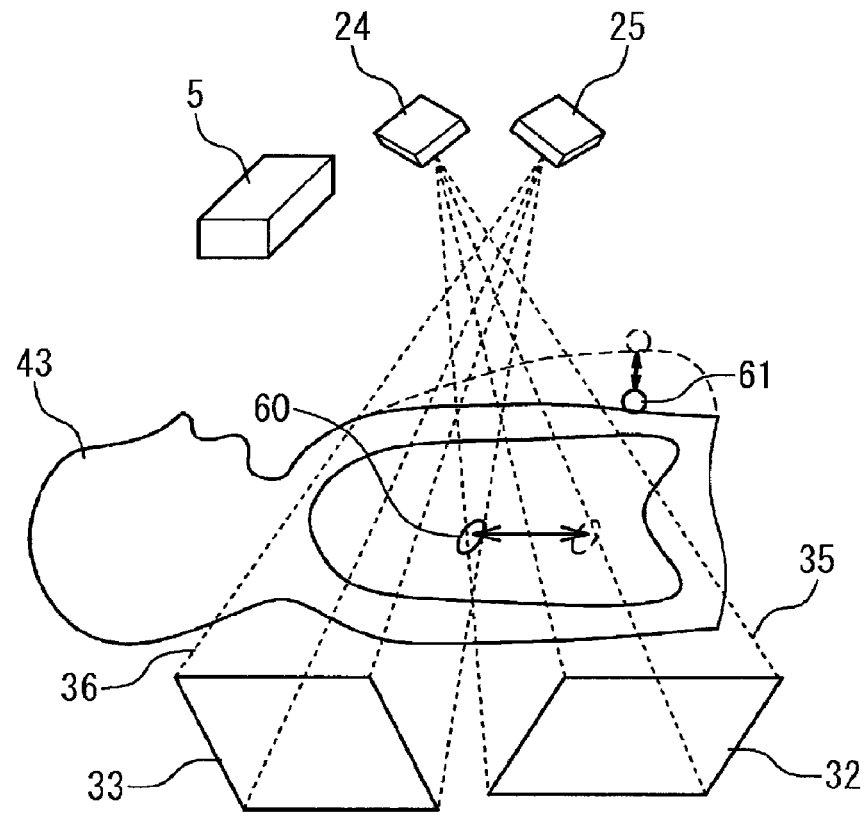
FIG. 4 is a cross-sectional view of the radiotherapy device according to the first embodiment of the present invention, which is taken while regarding a patient as centered.

FIG. 4 illustrates the patient 43. The patient 43 includes: an affected part 60; and a body surface maker 61. The affected part 60 is positioned inside the body of the patient 43, and moves in conjunction with breathing of the patient 43. The affected part 60 is shown on the transmissive image to be imaged by the imaging system. The body surface maker 61 is attached onto the surface of the body of the patient 43 so as to move in conjunction with the breathing of the patient 43. The body surface maker 61 is shown on the infrared image to be imaged by the infrared camera 5.

The infrared camera 5 is disposed so that the body surface maker 61 can be shown on an infrared image to be imaged, and is fixed to the base to which the radiotherapy device 3 is fixed.

At this time, based on the information input by the user through the input device, the trajectory model generator 51 fixes the O-ring 12 at the predetermined rotation angle by using the rotation driver 11 of the radiotherapy device 3, and fixes the travel gantry 14 at the predetermined travel angle by using the travel driver of the radiotherapy device 3 while regarding the rotation axis 18 as the center, so that the affected part 60 is more clearly shown on the transmissive image imaged by the imaging systems of the radiotherapy device 3. While the travel gantry 14 is fixed, the trajectory model generator 51 images, using the imaging systems of the radiotherapy device 3, a plurality of transmissive images of the patient 43 at a plurality of different imaging times. Then, the trajectory model generator 51 correlates the plurality of transmissive images with the plurality of imaging times, and stores in the storing unit, the plurality of transmissive images correlated with the plurality of imaging times. Additionally, the trajectory model generator 51 images, using the infrared camera 5, a plurality of infrared images of the patient 43 at the plurality of imaging times. Then, the trajectory model generator 51 correlates the plurality of infrared images with the plurality of imaging times, and stores in the storing unit, the plurality of infrared images correlated with the plurality of imaging times. Further, the trajectory model generator 51 calculates, based on the plurality of transmissive images, a trajectory of the affected part of the patient 43 which moves by the breathing of the patient 43. Moreover, the trajectory model generator 51 calculates, based on the plurality of transmissive images and the plurality of infrared images, a surrogate table indicating the relationship between the position of the body surface of the patient 43 and the position of the affected part of the patient 43.

The surrogate signal acquirer 54 images, using the infrared camera 5, an infrared image of the patient 43 simultaneously at the time that the transmissive image is imaged by the imager 52. Additionally, the surrogate signal acquirer 54 generates a surrogate signal value by image-processing the infrared image. The surrogate signal value corresponds to the position where the body surface maker 61 is shown on the infrared image.

Figure 5:
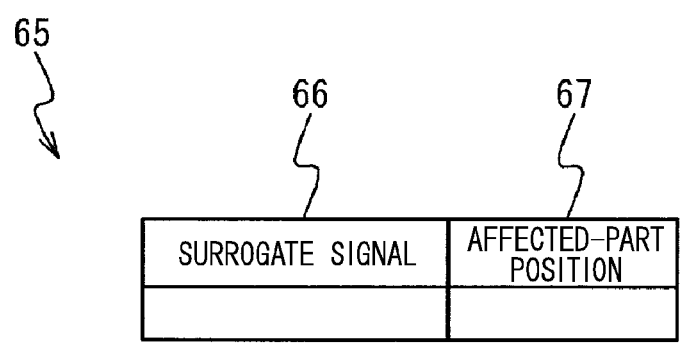
FIG. 5 is a diagram illustrating a surrogate table according to the first embodiment of the present invention.

FIG. 5 illustrates the surrogate table generated by the trajectory model generator 51. The surrogate table 65 correlates a set of surrogate signals 66 with a set of affected-part positions 67. In other words, any one of elements of the set of surrogate signals 66 is correlated with one of elements of the set of affected-part positions 67. Each of the elements of the set of surrogate signals 66 indicates a surrogate signal that can be collected by the surrogate signal acquirer 54. Each of the elements of the set of affected-part positions 67 indicates the position of a point included in the trajectory calculated by the trajectory model generator 51.

At this time, the trajectory model generator 51 generates the surrogate table 65 so that the position of the affected part 60 shown on the infrared image imaged using the infrared camera 5 corresponds to the position of the affected part 60 calculated by image-processing the transmissive image imaged by the imaging systems of the radiotherapy device 3.

At this time, the position calculator 55 refers to the surrogate table 65, and calculates one of the set of affected-part positions which is correlated with the surrogate signal value generated by the surrogate signal acquirer 54.

Figure 6:
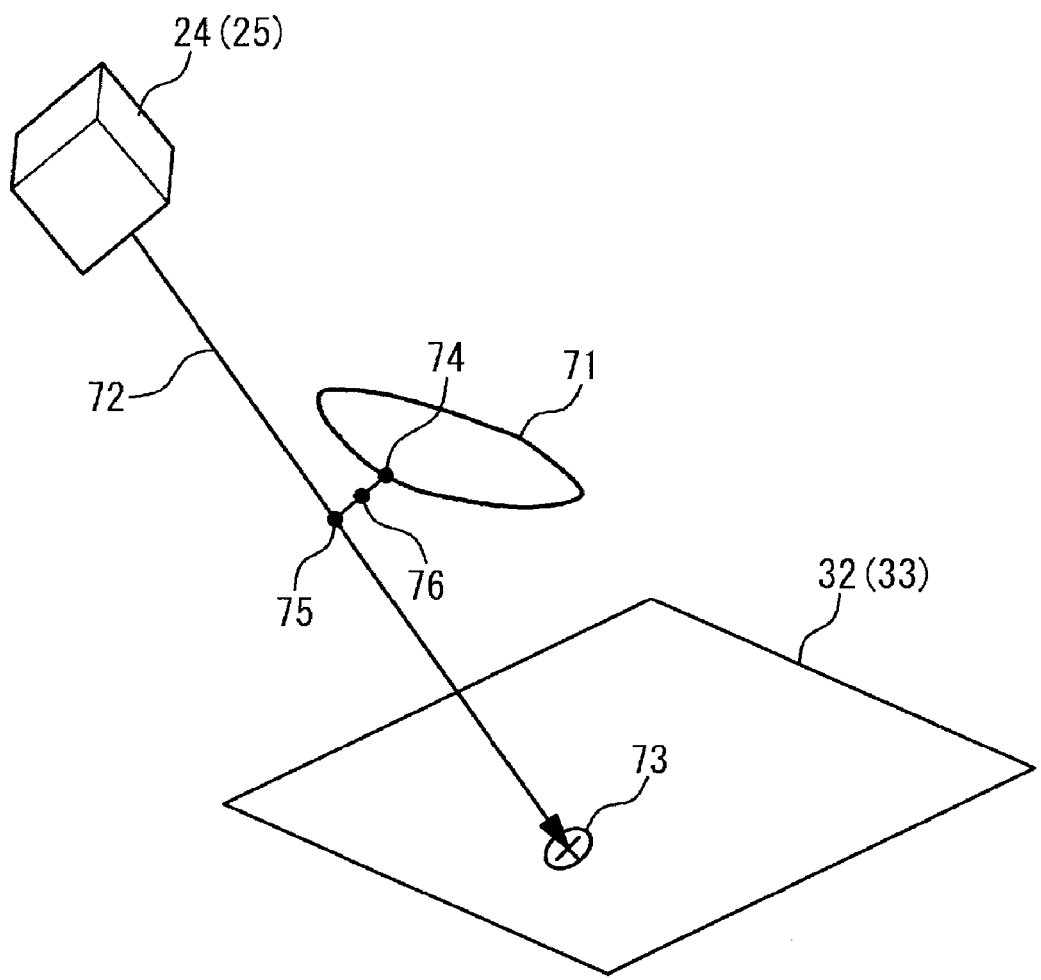
FIG. 6 is a perspective view illustrating the position of the patient for the radiotherapy device according to the first embodiment of the present invention.

FIG. 6 illustrates the trajectory calculated by the trajectory model generator 51. A trajectory 71 is formed in the shape of a smooth closed-curve. The trajectory 71 indicates the trajectory of the affected part 60, and includes elements of the set of affected-part positions 67 stored in the surrogate table 65.

FIG. 6 further illustrates the visual line calculated by the visual line calculator 53. A visual line 72 is calculated so as to pass through one point of the diagnostic X-ray source 24 and the affected part 60. In other words, the visual line 72 is formed as a line segment connecting the vertex of the diagnostic X-ray 35 emitted from the diagnostic X-ray source 24 and a point 73 on the sensor array 32. At this time, the point 73 is a point calculated by image-processing the transmissive image imaged using the diagnostic X-ray 35 and the sensor array 32, and corresponds to the position at which the affected part 60 is shown on the transmissive image. Alternatively, the visual line 72 is calculated so as to pass through one point of the diagnostic X-ray source 24 and the affected part 60. In other words, the visual line 72 is formed as a line segment connecting the vertex of the diagnostic X-ray 36 emitted from the diagnostic X-ray source 25 and the point 73 on the sensor array 33. At this time, the point 73 is a point calculated by image-processing the transmissive image imaged using the diagnostic X-ray 36 and the sensor array 33, and corresponds to the position at which the affected part 60 is shown on the transmissive image.

FIG. 6 further illustrates a plurality of points calculated by the position calculator 55. The plurality of points includes a first point 74, a second point 75, and a third point 76. The first point 74 is disposed at one of the set of affected-part positions 67 stored in the surrogate table 65, which is correlated with the surrogate signal value generated by the surrogate signal acquirer 54. The second point 75 indicates the point closest to the first point 74. The third point 76 indicates one of points included in the line segment connecting the first point 74 and the second point 75. The third point 76 indicates a point that internally divides the line segment at a ratio input by the user through the input device. Further, the third point 76 differs from the first point 74 and differs from the second point 75. The position calculator 55 calculates, as the position of the affected part, the position of one of the first point 74, the second point 75, and the third point 76, which is selected based on the information input by the user through the input device.

At this time, the emitter 58 controls the therapeutic radiation emitter 16 so as not to emit the therapeutic radiation 23 if the distance between the first point 74 and the second point 75 is greater than a predetermined threshold.

The radiation emitting method according to an embodiment of the present invention is executed by using the radiotherapy system 1 and includes: an operation of generating a trajectory of the affected part; and an operation of performing radiotherapy.

In the operation of generating the trajectory of the affected part, a user first fixes the patient 43 to the couch 41 of the radiotherapy device 3. Additionally, the user moves the couch 41 by operating the radiotherapy device controller 2 so that the position of the affected part 60 of the patient 43 substantially overlaps the isocenter 19. Further, the user fixes the O-ring 12 at the predetermined rotation angle by using the rotation driver 11 of the radiotherapy device 3, and fixes the travel gantry 14 at the predetermined travel angle by using the travel driver of the radiotherapy device 3 while regarding the rotation axis 18 as the center, so that the affected part 60 is more clearly shown on the transmissive image imaged by the imaging systems of the radiotherapy device 3. While the travel gantry 14 is fixed, the radiotherapy device controller 2 images, using the diagnostic X-ray source 24 and the sensor array 32, a plurality of transmissive images of the patient 43 at a plurality of different imaging times. Additionally, the radiotherapy device controller 2 images, using the diagnostic X-ray source 25 and the sensor array 33, a plurality of transmissive images of the patient 43 at the plurality of imaging times. Further, the radiotherapy device controller 2 images, using the infrared camera 5, a plurality of infrared images of the patient 43 at the plurality of imaging times. Moreover, the radiotherapy device controller 2 calculates, based on the plurality of transmissive images, the trajectory 71 of the affected part 60 of the patient 43, which moves in conjunction with breathing of the patient 43. Additionally, the radiotherapy device controller 2 calculates the surrogate table 65 based on the plurality of transmissive images and the plurality of infrared images.

Figure 7:
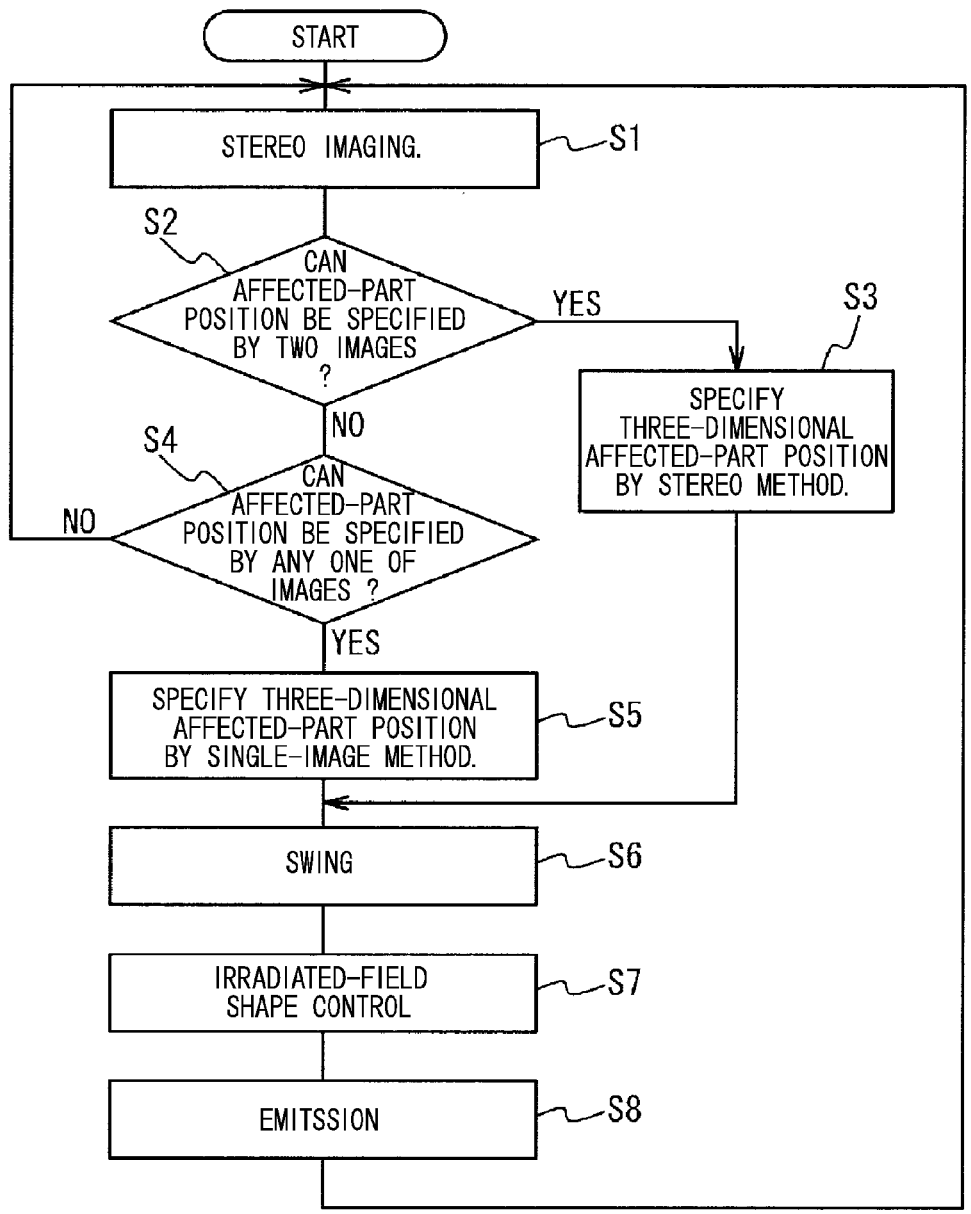
FIG. 7 is a flowchart illustrating operations of radiotherapy according to the first embodiment of the present invention.

FIG. 7 illustrates operations of performing radiotherapy. The operations of performing radiotherapy are executed immediately after the operation of generating the trajectory of the affected part. The operations of performing radiotherapy are executed while the patient 43 has remained fixed since the operation of generating the trajectory of the affected part thereof. The radiotherapy device controller 2 fixes, using the rotation driver 11 of the radiotherapy device 3, the O-ring 12 at the rotation angle indicated by the therapy plan. Additionally, the radiotherapy device controller 2 fixes, using the travel driver of the radiotherapy device 3, the travel gantry 14 at the travel angle specified by the therapy plan.

While the travel gantry 14 is fixed, the radiotherapy device controller 2 images a transmissive image of the patient 43 by using the diagnostic X-ray source 24 and the sensor array 32. Additionally, the radiotherapy device controller 2 images a transmissive image of the patient 43 by using the diagnostic X-ray source 25 and the sensor array 33. Further, the radiotherapy device controller 2 images an infrared image of the patient 43 by using the infrared camera 5 (step S1). The radiotherapy device controller 2 determines whether or not the position of the affected part 60 can be specified based on the transmissive image imaged by using the diagnostic X-ray source 24 and the sensor array 32, and the transmissive image by using the diagnostic X-ray source 25 and the sensor array 33 (step S2).

If the position of the affected part 60 can be specified based on the two transmissive images, in other words, if both the two transmissive images clearly show the affected part 60 (step S2: Yes), the radiotherapy device controller 2 specifies the position of the affected part 60 in a stereo method (i.e., based on the two transmissive images) (step S3).

If the position of the affected part 60 cannot be specified based on the two transmissive images (step S2: No), the radiotherapy device controller 2 determines whether or not one of the two transmissive images clearly shows the affected part 60 (step S4). If both the two transmissive images do not clearly show the affected part 60 (step S4: No), the radiotherapy device controller 2 performs the operations from the step S1 again.

If one of the two transmissive images clearly shows the affected part 60 (step S4: Yes), the radiotherapy device controller 2 calculates the position of the affected part in a single method (step S5). In other words, the radiotherapy device controller 2 calculates the visual line 72 based on the one of the transmissive images. Additionally, the radiotherapy device controller 2 calculates a surrogate signal value based on the infrared image thereof. Then, the radiotherapy device controller 2 refers to the surrogate table 65, and thereby calculates the first point 74 of the set of affected-part positions, which is correlated to the surrogate signal value thereof. Further, the radiotherapy device controller 2 calculates the second point 75 which is included in the visual line 72 and closest to the first point 74. Moreover, the radiotherapy device controller 2 calculates the third point 76 that internally divides the line segment connecting the first point 74 and the second point 75 at the ratio input by the user through the input device. Additionally, the radiotherapy device controller 2 calculates, as the position of the affected part, one of the first point 74, the second point 75, and the third point 76, which is selected based on the information previously input by the user through the input device.

Based on the position of the affected part calculated by the stereo method or the position of the affected part calculated by the single method, the radiotherapy device controller 2 controls the swing mechanism 15 so that the irradiation axis of the therapeutic radiation 23 passes through the position of the affected part (step S6). Additionally, the radiotherapy device controller 2 calculates the shape of the irradiated field based on the transmissive image thereof. Then, the radiotherapy device controller 2 controls the multileaf collimator 20 so that the irradiated field of the therapeutic radiation 23 is formed in the calculated shape (step S7). Further, the radiotherapy device controller 2 emits the therapeutic radiation 23 to the patient by using the therapeutic radiation emitter 16 (step S8). At this time, the radiotherapy device controller 2 controls the therapeutic radiation emitter 16 so as not to emit the therapeutic radiation 23 if the distance between the first point 74 and the second point 75 is greater than the predetermined threshold.

The radiotherapy device controller 2 periodically repeats the operations from the step S1 to the step S8 until the dose of the therapeutic radiation 23 emitted to the patient 43 becomes the dose specified by the therapy plan.

The radiotherapy device controller 2 cannot precisely calculate the position of the affected part 60 of the patient 43 based on only one of the two transmissive images imaged in step S1. According to the above operations of performing radiotherapy, the radiotherapy device controller 2 can calculate the position of the affected part 60 with high precision while one of the two transmissive images imaged in the step S1 shows the affected part 60. Accordingly, the radiotherapy system 1 can more precisely calculate the position of the affected part 60.

If the distance between the first point 74 and the second point 75 is greater than the predetermined threshold, there is a possibility that the position of the affected part will not be calculated adequately. For this reason, the therapeutic radiation emitter 16 is controlled so as not to emit the therapeutic radiation 23 if the distance between the first point 74 and the second point 75 is greater than the predetermined threshold, thereby further enhancing reliability.

The positions of the imaging systems configured to image transmissive images to calculate the trajectory 71 are independent from the position of the therapeutic radiation emitter 16 to be disposed at the time of radiotherapy. Accordingly, the trajectory 71 can be more properly calculated with higher precision, which is more preferable.

In the operations of performing radiotherapy, only one of the imaging systems may be operated to calculate the position of the affected part. Even in this case, the position of the affected part 60 can be similarly calculated with high precision. Accordingly, the radiotherapy system 1 can treat by radiotherapy the patient 43 with higher precision. At this time, the exposed level of the radiation emitted to the patient 43 can be reduced, which is more preferable.

The trajectories 71, 82, and 91 can be calculated by using another device other than the imaging systems of the radiotherapy device 3. Such a device includes an MRI and a 4D-CT. Even if the trajectory calculated by another device is used, the radiotherapy device controller 2 can similarly calculate the position of the affected part of the patient 60 with higher precision while one of the two transmissive images imaged in the step S1 shows the affected part 60. Accordingly, the radiotherapy system 1 can treat by radiotherapy the patient 43 with higher precision.

The infrared camera 5 may be replaced with another sensor that measures a phase of breathing without using radiation penetrating the patient 43. Such a sensor includes a spirometer that measures the volume of ventilation when a patient breathes. Even if such a sensor is included, the radiotherapy device controller 2 can similarly calculate the position of the affected part of the patient 60 with higher precision while one of the two transmissive images imaged in the step S1 shows the affected part 60. Accordingly, the radiotherapy system 1 can treat by radiotherapy the patient 43 with higher precision.

Figure 8:
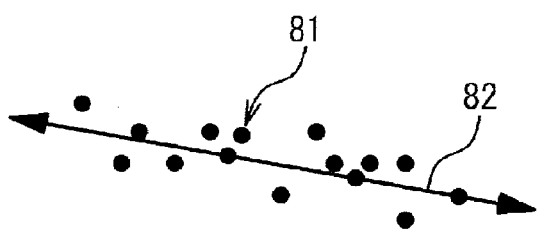
FIG. 8 is a plan view illustrating another trajectory.

FIG. 8 illustrates another trajectory calculated by the trajectory model generator 51. A trajectory 82 includes a line segment, and is calculated based on a plurality of points 81 calculated from a plurality of transmissive images imaged at a plurality of respective times by the imaging systems of the radiotherapy device 3. The plurality of points 81 indicate the positions where the affected part 60 has been disposed at the plurality of respective times. The trajectory 82 indicates a line segment approximated from the plurality of points 81. A least square method is used as a method of generating such a trajectory as the trajectory 82.

Figure 9:
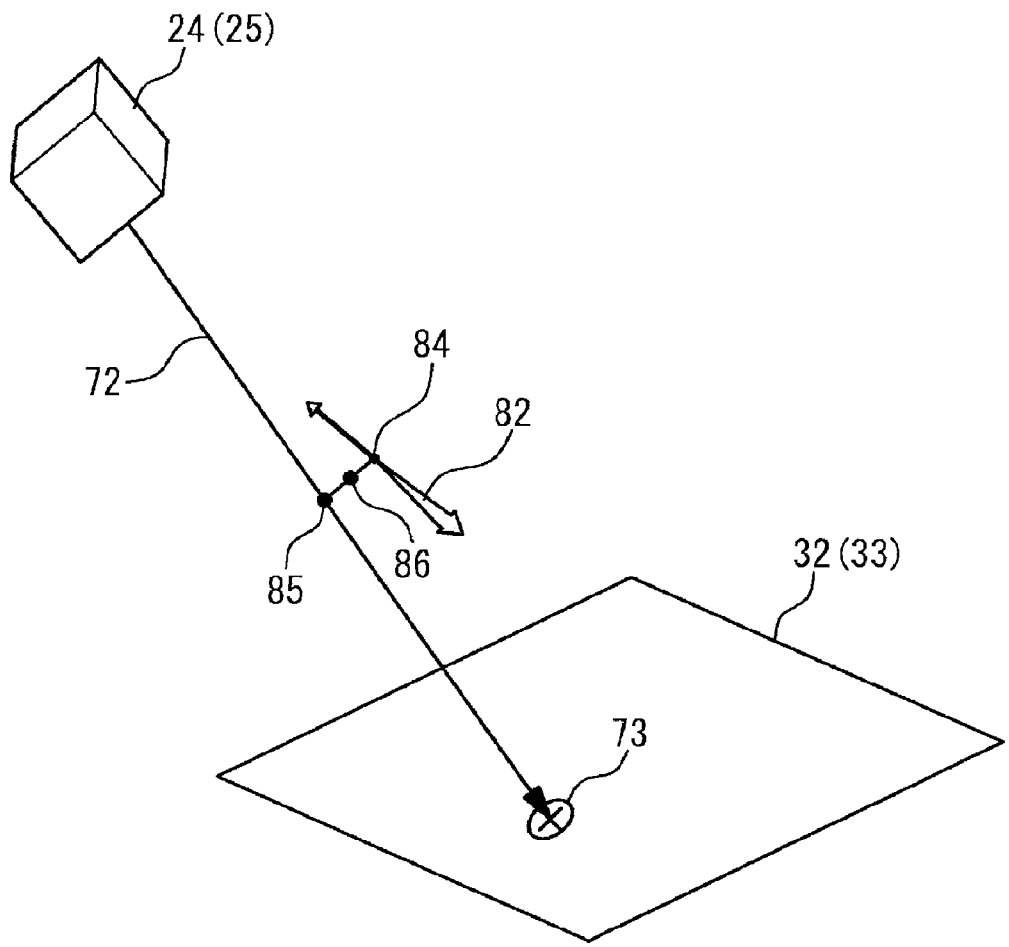
FIG. 9 is a perspective view illustrating another position of the patient.

FIG. 9 illustrates a plurality of points calculated by the position calculator 55 when such a trajectory as the trajectory 82 is used. The plurality of points include the first point 84, the second point 85, and the third point 86. The first point 84 indicates the point closest to the visual line 72. The second point 85 indicates the point which is included in the visual line 72 and is the closest to the first point 84. The third point 86 indicates a point included in a line segment connecting the first point 84 and the second point 85. The third point 86 indicates the point that internally divides the line segment at the ratio input by the user through the input device. The third point 86 differs from the first point 84 and differs from the second point 85. The position calculator 55 calculates, as the position of the affected part, the position of one of the first point 84, the second point 85, and the third point 86, which is selected based on the information input by the user through the input device.

The position of the affected part calculated in such a manner is lower in precision than the position of the affected part calculated using a surrogate signal. However, such a position of the affected part can be calculated without necessitating the surrogate signal and the surrogate table 65. For this reason, the position calculator 55 can calculate the position of the affected part more easily and more quickly. At this time, the radiotherapy system 1 does not need the infrared camera 5 to calculate the position of the affected part. For this reason, the radiotherapy system 1 can omit the infrared camera 5, and therefore can be manufactured at a lower cost. If the trajectory 82 is a curve, a plurality of first points 84, which are included in the trajectory 82 and the closest to the visual line 72, are calculated in some cases. If the trajectory 82 is approximated by a line segment, a unique first point 84 can be calculated properly, which is more preferable.

Figure 10:
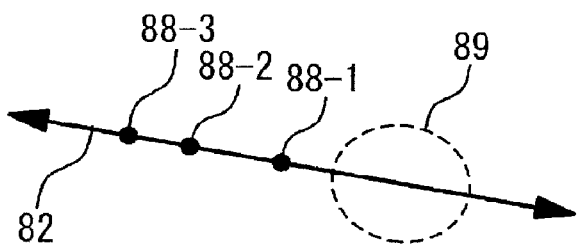
FIG. 10 is a perspective view illustrating still another trajectory.

At this time, the emitter 58 controls the therapeutic radiation emitter 16 so as not to emit the therapeutic radiation 23 if the distance between the first point 84 and the second point 85 is greater than the predetermined threshold. Additionally, the emitter 58 calculates a region 89 based on the positions of the affected part 88-1 to 88-3 which are previously calculated by the position calculator 55, as shown in FIG. 10. The region 89 indicates a region in which the position of an affected part to be calculated next is estimated to be present. If the position of the affected part calculated next by the position calculator 55 is not included in the region 89, the emitter 58 controls the therapeutic radiation emitter 16 so as not to emit the therapeutic radiation 23. If the calculated position of the affected part is not included in the region 89, there is a high possibility that the position of the affected part is not adequately calculated. For this reason, according to such a control, the radiotherapy system 1 can further enhance reliability.

Figure 11:
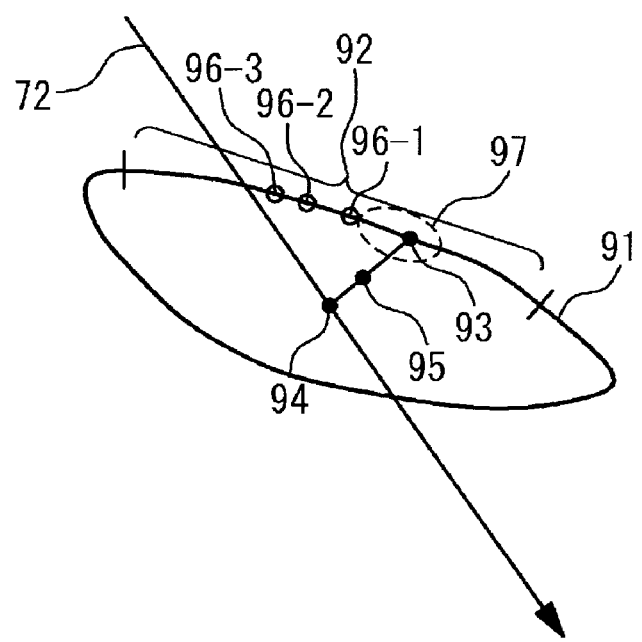
FIG. 11 is a perspective view illustrating still another position of the patient.

FIG. 11 illustrates another trajectory calculated by the trajectory model generator 51. A trajectory 91 is formed to be a smooth closed line, and is divided into a plurality of portions. At this time, the surrogate table calculated by the trajectory model generator 51 correlates the set of surrogate signals 66 with a set of partial trajectories. In other words, any one of elements of the set of surrogate signals 66 is correlated with one of the elements of the set of partial trajectories. Each of the elements of the set of partial trajectories indicates one of divided portions of the trajectory 91.

At this time, the position calculator 55 refers to the surrogate table 65, and calculates a partial trajectory 92 which is included in the set of affected-part positions 67 and is correlated with the surrogate signal value generated by the surrogate signal acquirer 54. The position calculator 55 calculates the first point 93, the second point 94, and the third point 95 based on the partial trajectory 92 and the visual line 72. The first point 93 indicates a point which is included in the visual line 72 and closest to the first point 93. The third point 95 indicates one point included in a line segment connecting the first point 93 and the second point 94. The third point 95 indicates a point that internally divides the line segment at the ratio input by the user through the input device. Additionally, the third point 95 differs from the first point 93 and differs from the second point 94. The position calculator 55 calculates, as the position of the affected part, the position of one of the first point 93, the second point 94, and the third point 95, which is selected by the information input by the user through the input device.

If the trajectory 91 is a curve, a plurality of first points 93, which are included in the trajectory 91 and are closest to the visual line 72, are calculated in some cases. Additionally, a plurality of second points 94, which are included in the visual line 72 and closest to the trajectory 91, are calculated in some cases. If the first point 93 is calculated from the partial trajectory 92 included in the trajectory 91, the first point 93 can be calculated uniquely and properly, which is more preferable.

At this time, the emitter 58 controls the therapeutic radiation emitter 16 so as to emit the therapeutic radiation 23 to the position of the affected part calculated by the position calculator 55. However, the emitter 58 may control, based on the result of the calculation previously performed by the position calculator 55, the therapeutic radiation emitter 16 so as not to emit the therapeutic radiation 23. For example, the emitter 58 may control the therapeutic radiation emitter 16 so as not to emit the therapeutic radiation 23 if the distance between the first point 93 and the second point 94 is greater than the predetermined threshold. Additionally, the emitter 58 calculates a region 97 based on the positions of the affected part 96-1 to 96-3 which are previously calculated by the position calculator 55. The region 97 indicates a region in which the position of the affected part to be calculated next is estimated to be present. If the position of the affected part calculated next by the position calculator 55 (one point selected from the first point 93, the second point 94, and the third point 95) is not included in the region 97, the emitter 58 controls the therapeutic radiation emitter 16 so as not to emit the therapeutic radiation 23. For this reason, according to such a control, the radiotherapy system 1 can further enhance reliability, in a similar manner to the above control explained with reference to FIG. 10.

The method of measuring the position of a specific part according to the present invention is applicable to the gating radiation. In this case, if the position of the affected part calculated by the position calculator 55 is within a predetermined region, the emitter 58 controls the therapeutic radiation emitter 16 so as to emit the therapeutic radiation 23 to the patient. If the position of the affected part calculated by the position calculator 55 is not within the predetermined region, the emitter 58 controls the therapeutic radiation emitter 16 so as not to emit the therapeutic radiation 23 to the patient. Even in this case, the radiotherapy system 1 can similarly calculate the position of the affected part of the patient 60 with higher precision, treat by radiotherapy the patient 43 with high precision, and reduce the exposed level of radiation to be emitted to the patient 43.

INDUSTRIAL APPLICABILITY

According to the radiotherapy device controller and the method of measuring the position of a specific part of the present invention, the position of a specific part included inside a subject can be measured with higher precision. Additionally, when the position of the specific part is calculated using one transmissive image, the exposed level of radiation emitted to the subject can be reduced compared to the technique of calculating the position of the specific part using a plurality of transmissive images.

DESCRIPTION OF REFERENCE NUMERALS

1: radiotherapy system
2: radiotherapy device controller

3: radiotherapy device
5: infrared camera
11: rotation driver
12: O-ring
14: travel gantry
15: swing mechanism
16: therapeutic radiation emitter
17: rotation axis
18: rotation axis
19: isocenter
20: multileaf collimator
21: tilt axis
22: pan axis
23: therapeutic radiation
24: diagnostic X-ray source
25: diagnostic X-ray source
32: sensor array
33: sensor array
35: diagnostic X-ray
36: diagnostic X-ray
41: couch
42: couch driver
43: patient
51: trajectory model generator
52: imager
53: visual line calculator
54: surrogate signal acquirer
55: position calculator
56: swing driver
58: emitter
60: affected part
61: body-surface marker
65: surrogate table
66: set of surrogate signals
67: set of affected-part positions
71: trajectory
72: visual line
73: point
74: first point
75: second point
76: third point
81: a plurality of points
82: trajectory
84: first point
85: second point
86: third point
88-1: position of affected part
88-2: position of affected part
88-3: position of affected part
89: region
91: trajectory
92: partial trajectory
93: first point
94: second point
95: third point
96-1: position of affected part
96-2: position of affected part
96-3: position of affected part
97: region

The invention claimed is:

1. A radiotherapy device controller comprising:
a visual line calculating circuit configured to calculate a visual line connecting a source of a first radiation penetrating a subject and a first position of a specific part inside the subject, the first position being shown on a transmissive image captured using the first radiation, and the visual line being different from a radiation line of the first radiation;
a position calculating circuit configured to calculate a second position of the specific part based on a first point on a trajectory of the specific part and a second point on the visual line, the trajectory being described along with movement of the subject and calculated based on a plurality of transmissive images captured using radiations other than the first radiation, and the first point and the second point being selected so as to minimize a distance between the first point and the second point; and
an emitting circuit configured to control a radiation emitting device that emits a therapeutic radiation, so that the therapeutic radiation penetrates at the second position of the specific part.

2. The radiotherapy device controller according to claim 1, wherein the second position of the specific part indicates a position of a third point included in a line segment connecting the first point and the second point,
the first point is included in the trajectory and is closest to the visual line, and
the second point is included in the visual line and is closest to the trajectory.

3. The radiotherapy device controller according to claim 2, wherein the trajectory is formed to be a line segment.

4. The radiotherapy device controller according to claim 1, further comprising:
a trajectory model generating circuit configured to calculate the trajectory based on the plurality of transmissive images, the plurality of transmissive images including a plurality of first transmissive images and a plurality of second transmissive images, the plurality of first transmissive images being captured at a plurality of different times by using a second radiation emitted from a third position, and the plurality of second transmissive images being captured at the plurality of different times by using a third radiation emitted from a fourth position different from the third position.

5. The radiotherapy device controller according to claim 1, further comprising:
a surrogate signal acquiring circuit configured to collect a plurality of surrogate signal values measured at a plurality of times the plurality of transmissive images are captured,
wherein the position calculating circuit is configured to refer to a table that correlates a set of surrogate signal values with a set of partial trajectories, and to calculate from the set of partial trajectories, a partial trajectory correlated with one of the plurality of surrogate signal values,
the trajectory includes the partial trajectory,
the second position of the specific part indicates a position of a third point included in a line segment connecting the first point and the second point,
the first point is included in the partial trajectory and is closest to the visual line, and
the second point is included in the visual line and is closest to the partial trajectory.

6. The radiotherapy device controller according to claim 4, further comprising:
a surrogate signal acquiring circuit configured to collect a plurality of surrogate signal values measured at the plurality of different times the plurality of first transmissive images are captured,
wherein the position calculating circuit is configured to refer to a table that correlates a set of surrogate signal values with a set of positions, and to calculate the first point that is included in the set of positions and is correlated with one of the plurality of surrogate signal values, the second position of the specific part indicates a position of a third point included in a line segment connecting the first point and the second point, the second point is included in the visual line and is closest to the first point, and the third point differs from the first point.

7. The radiotherapy device controller according to claim 5, wherein each of the plurality of surrogate signal values indicates a position of a marker on the subject, and the marker differs from the specific part.

8. The radiotherapy device controller according to claim 5, wherein the second position of the specific part indicates a position of a point selected from the first point, the second point, and the third point based on information input by an input device, the third point differs from the first point, and the third point differs from the second point.

9. The radiotherapy device controller according to claim 1, further comprising:

a driving circuit configured to drive, based on the second position of the specific part, a driving device that drives the radiation emitting device, so that the therapeutic radiation penetrates at the second position of the specific part.

10. The radiotherapy device controller according to claim 9, wherein the emitting circuit is configured to calculate a region based on a previous position of the specific part calculated before the second position of the specific part is calculated, and the emitting circuit is configured to control the radiation emitting device so as not to emit the therapeutic radiation if the second position of the specific part is not included in the region.

11. The radiotherapy device controller according to claim 1, further comprising:

an irradiated-field shape control circuit configured to control, based on the transmissive image, an irradiated-field shape control device that partially blocks the therapeutic radiation.

12. A method of measuring a position of a specific part, comprising:

calculating a visual line connecting a source of a first radiation penetrating a subject and a first position of a specific part inside the subject, the first position being shown on a transmissive image captured using the first radiation, and the visual line being different from a radiation line of the first radiation; and calculating a second position of the specific part based on a first point on a trajectory of the specific part and a second point on the visual line, the trajectory being described along with movement of the subject and calculated based on a plurality of transmissive images captured using radiations other than the first radiation, and the first point and the second point being selected so as to minimize a distance between the first point and the second point.

13. The method of measuring the position of the specific part according to claim 12, wherein the second position of the specific part indicates a position of a third point included in a line segment connecting the first point and the second point, the first point is included in the trajectory and is closest to the visual line, and the second point is included in the visual line and is closest to the trajectory.

14. The method of measuring the position of the specific part according to claim 13, wherein the trajectory is formed to be a line segment.

15. The method of measuring the position of the specific part according to claim 12, further comprising:

calculating the trajectory based on the plurality of transmissive images, the plurality of transmissive images including a plurality of first transmissive images and a plurality of second transmissive images, the plurality of first transmissive images being captured at a plurality of different times by using a second radiation emitted from a third position, and the plurality of second transmissive images being captured at the plurality of different times by using a third radiation emitted from a fourth position different from the third position.

16. The method of measuring the position of the specific part according to claim 15, further comprising:

generating a table that correlates a set of surrogate signal values with a set of partial trajectories, based on the trajectory and a plurality of surrogate signal values measured at the plurality of different times;

collecting a plurality of surrogate signal values measured at the plurality of different times the plurality of transmissive images are captured; and calculating from the set of partial trajectories, a partial trajectory correlated with one of the plurality of surrogate signal values, wherein the second position of the specific part indicates a position of a third point included in a line segment connecting the first point and the second point, the first point is included in the partial trajectory and is closest to the visual line, and the second point is included in the visual line and is closest to the partial trajectory.

17. The method of measuring the position of the specific part according to claim 15, further comprising:

generating a table that correlates a set of surrogate signal values with a set of positions, based on the trajectory and a plurality of surrogate signal values measured at the plurality of different times;

collecting a plurality of surrogate signal values measured at the plurality of different times the plurality of first transmissive images are captured; and calculating the first point that is included in the set of positions and is correlated with one of the plurality of surrogate signal values, wherein the second position of the specific part indicates a position of a third point included in a line segment connecting the first point and the second point, the second point is included in the visual line and is closest to the first point, and the third point differs from the first point.

18. A radiation emitting method comprising:

calculating a visual line connecting a source of a first radiation penetrating a subject and a first position of a specific part inside the subject, the first position being shown on a transmissive image captured using the first radiation, and the visual line being different from a radiation line of the first radiation;

calculating a second position of the specific part based on a first point on a trajectory of the specific part and a second point on the visual line, the trajectory being described along with movement of the subject and calculated based on a plurality of transmissive images captured using radiations other than the first radiation, and the first point and the second point being selected so as to minimize a distance between the first point and the second point; and controlling a radiation emitting device that emits a therapeutic radiation, so that the therapeutic radiation penetrates at the second position of the specific part.

19. The radiation emitting method according to claim 18, further comprising:

calculating a region based on a previous position of the specific part before calculating the second position of the specific part, the precious position being calculated by calculating the visual line and calculating the second position of the specific part; and controlling the radiation emitting device so as not to emit the therapeutic radiation if the second position of the specific part is not included in the region.

20. The radiation emitting method according to claim 18, further comprising:

controlling, based on the transmissive image, an irradiated-field shape control device that partially blocks the therapeutic radiation.

* * * * *